US006926408B2

(12) United States Patent
Sarver

(10) Patent No.: US 6,926,408 B2
(45) Date of Patent: Aug. 9, 2005

(54) CONTINUOUS TWO-DIMENSIONAL CORNEAL TOPOGRAPHY TARGET

(75) Inventor: Edwin J. Sarver, Celebration, FL (US)

(73) Assignee: Sarver & Associates Inc., Carbondale, IL (US)

(*) Notice: Subject to any disclaimer, the term of this patent is extended or adjusted under 35 U.S.C. 154(b) by 68 days.

(21) Appl. No.: 10/446,172

(22) Filed: May 23, 2003

(65) Prior Publication Data

US 2004/0027537 A1 Feb. 12, 2004

Related U.S. Application Data

(60) Provisional application No. 60/382,722, filed on May 24, 2002.

(51) Int. Cl.[7] ................................................ A61B 3/10
(52) U.S. Cl. ...................................................... 351/212
(58) Field of Search ................................ 351/200, 205, 351/211, 212, 221, 246; 600/558

(56) References Cited

U.S. PATENT DOCUMENTS

| 4,493,539 | A | * | 1/1985 | Cannon, Jr. ................. 351/211 |
| 4,863,260 | A | * | 9/1989 | Gersten et al. ............. 351/212 |
| 4,995,716 | A | * | 2/1991 | Warnicki et al. ............ 351/212 |
| 5,841,511 | A | * | 11/1998 | D'Souza et al. ............ 351/212 |
| 5,912,723 | A | * | 6/1999 | Maddess ..................... 351/211 |

* cited by examiner

*Primary Examiner*—Max F. Hindenburg
*Assistant Examiner*—John R Sanders
(74) *Attorney, Agent, or Firm*—McHale & Slavin PA

(57) ABSTRACT

A means to generate a continuous two-dimensional reflection pattern suitable for corneal topography that uses sinusoidal profiles of both intensity and color values. The technique provides a more robust image processing due to the ability to apply digital band pass filters, continuous data for improved surface reconstruction, and the ability to directly measure the meridian of the reflection pattern source point when the corneal surface normal does not lie in the meridian of the measurement instrument.

15 Claims, 4 Drawing Sheets

CONTINUOUS TWO-DIMENSIONAL CORNEAL TOPOGRAPHY TARGET

RELATED APPLICATIONS

This application is a continuation of U.S. Provisional Application 60/382,722 filed May 24, 2002 and claims priority thereto.

FIELD OF THE INVENTION

This invention is directed to the field of eye examination.

BACKGROUND OF THE INVENTION

The human cornea provides about two-thirds of the refraction of the eye. Thus, its shape is of great interest to optometrists and ophthalmologists who must provide a patient with sharp vision. A device that measures the shape of the cornea is referred to as a corneal topographer. Although there are various methods to measure the cornea, the most popular commercial systems are based on the principle of measuring a pattern reflected off the cornea. The pattern most often used for this purpose is a set of concentric rings. One problem with concentric ring patterns is that it is difficult to know the exact point correspondence between a point on the reflected pattern source and its image reflected off the cornea. If the cornea is not axially symmetric, the surface normal of a point on the cornea will not lie in the meridional plane of the measurement system and thus, the point of light originating on the reflected pattern source will not lie in the same meridional plane. To directly measure the point correspondence, polar and rectangular checkerboard patterns have also been proposed, but have not become popular in commercial systems.

Usually these various reflection patterns are monochrome (black and white), but color has been included in some cases. In one commercial system concentric rings are of alternating colors of red, green, and blue. In a research system, a random color grid was employed. In cases where color is used, the motivation is to provide a more robust method of correctly identifying the correspondence between a point on the reflection pattern source and the image reflected off the cornea and digitized for computer processing.

The reflection patterns to date have been discrete in some way and the computer image processing task is to find edges or peaks in the image which correspond to points in the source. The results of the computer image processing can yield a set of point correspondences that is not always correct. Such image processing errors would lead to large measurement errors in subsequent reconstruction processing. Even if the point correspondence is correct, the accuracy of reconstruction algorithms is related to the spacing of the data. Generally, if the discrete points are far apart the reconstruction error will be larger than would be obtained if the points were close together. Because of this general observation, continuous data would provide the most accurate surface reconstruction measurements.

SUMMARY OF THE INVENTION

The aim of this invention is to provide a means to generate a continuous two-dimensional reflection pattern suitable for corneal topography that uses sinusoidal profiles of both intensity and color values. The benefits of this technique are more robust image processing due to the ability to apply digital band pass filters, continuous data for improved surface reconstruction, and the ability to directly measure the meridian of the reflection pattern source point when the corneal surface normal does not lie in the meridian of the measurement instrument.

Other objects and advantages of this invention will become apparent from the following description taken in conjunction with the accompanying drawings wherein are set forth, by way of illustration and example, certain embodiments of this invention.

DETAILED DESCRIPTION

Figure 1:
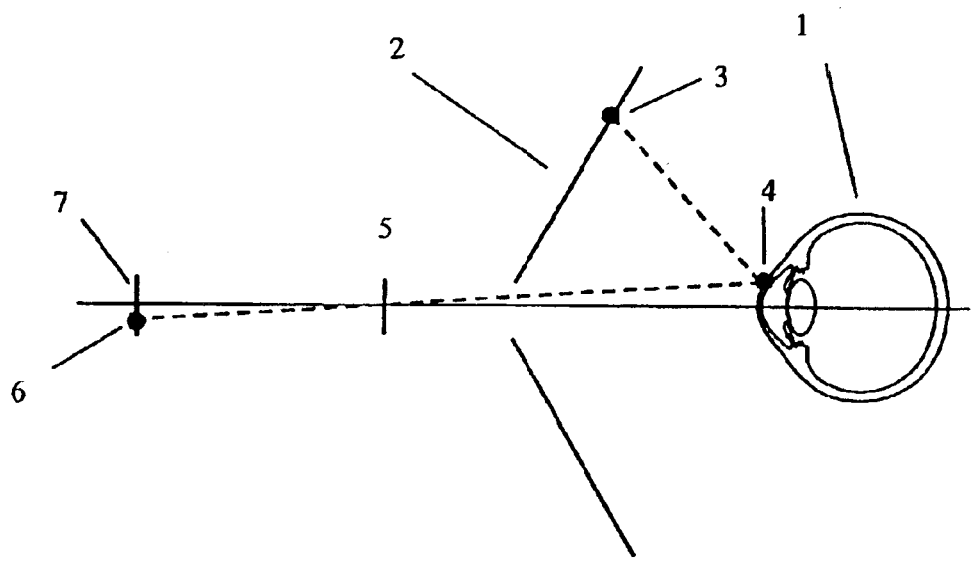
FIG. 1 illustrates the basic geometry for a reflection based corneal topography system.
Figure 2:
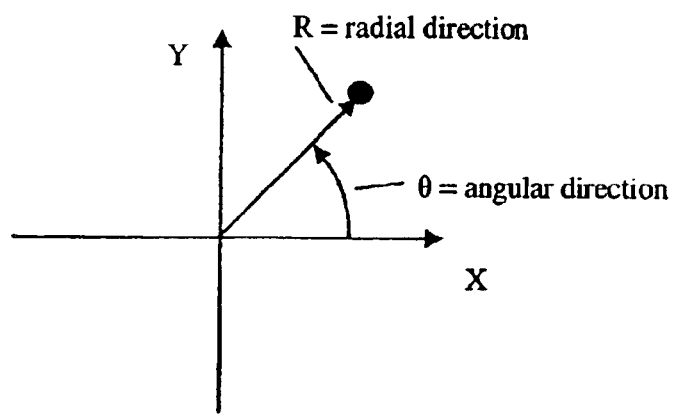
FIG. 2 illustrates the coordinate system for referring to the reflection target pattern.

The basic geometry for a reflection based corneal topography system is illustrated in FIG. 1. The eye 1 is positioned in front of the reflection pattern source 2. A point 3 on the reflection source reflects off the cornea at corneal surface point 4 and is focused by lens 5 onto CCD sensor 7 at digital image point 6. The proposed reflection pattern consists of three parts: the radial intensity profile, the angular color profile, and the contrast control.

Radial Intensity Profile

The radial intensity profile is given by equation (1).

$$I(r,t) = \begin{cases} 0 & r < r0 \\ \dfrac{\cos\left[\dfrac{(r-r0)\times 2\pi \times Nr}{r\mathrm{Max}-r0} + t\times Nt + \pi\right]}{2} + \dfrac{1}{2} & r0 < r < r\mathrm{Max} \\ 0 & r > r\mathrm{Max} \end{cases}$$

where r0=radial starting point (mm)

rMax=radial ending point (mm)

Nr=radial cycles

Nt=spiral cycles

Figure 3:
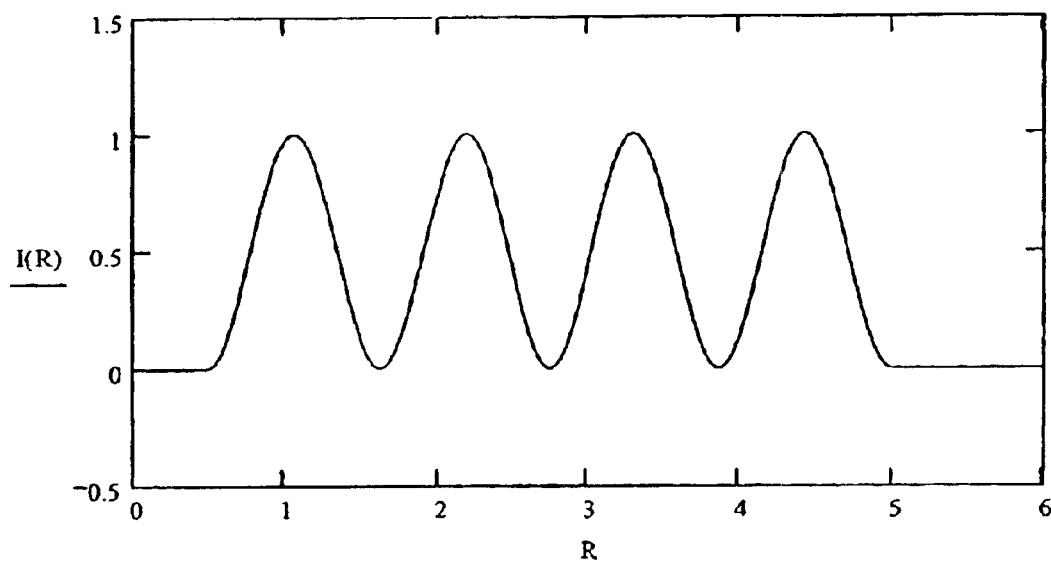
FIG. 3 shows an example of a graph of the intensity profile of the reflection target pattern as a function of the radial distance.
Figure 5:
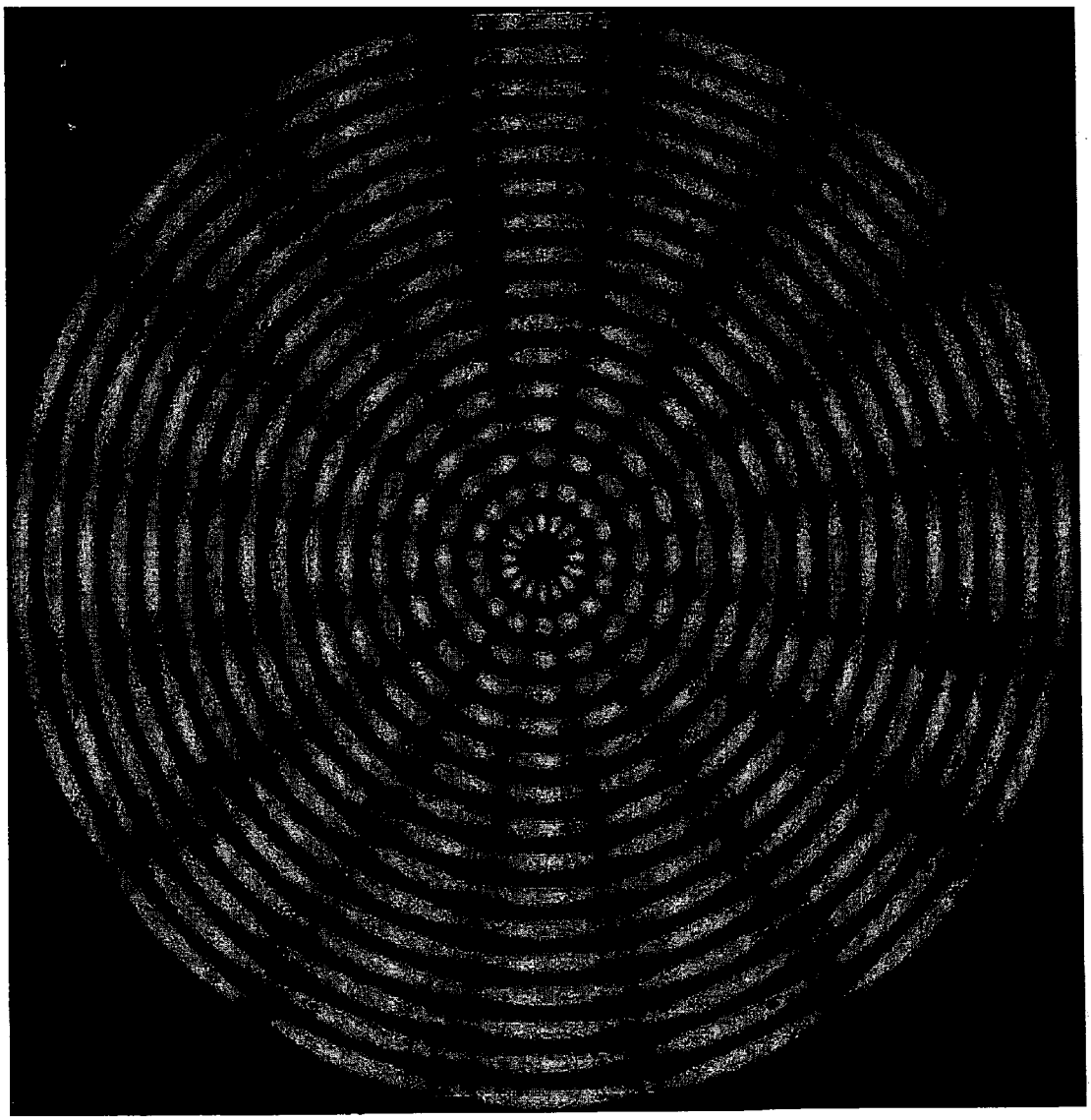
FIG. 5 shows an example of the preferred reflection target pattern in which the intensity profile is the same for all angles and the red, green, and blue profiles have the same frequency but have phase values of 0, 2*PI/3, and 4*PI/3, respectively.
Figure 6:
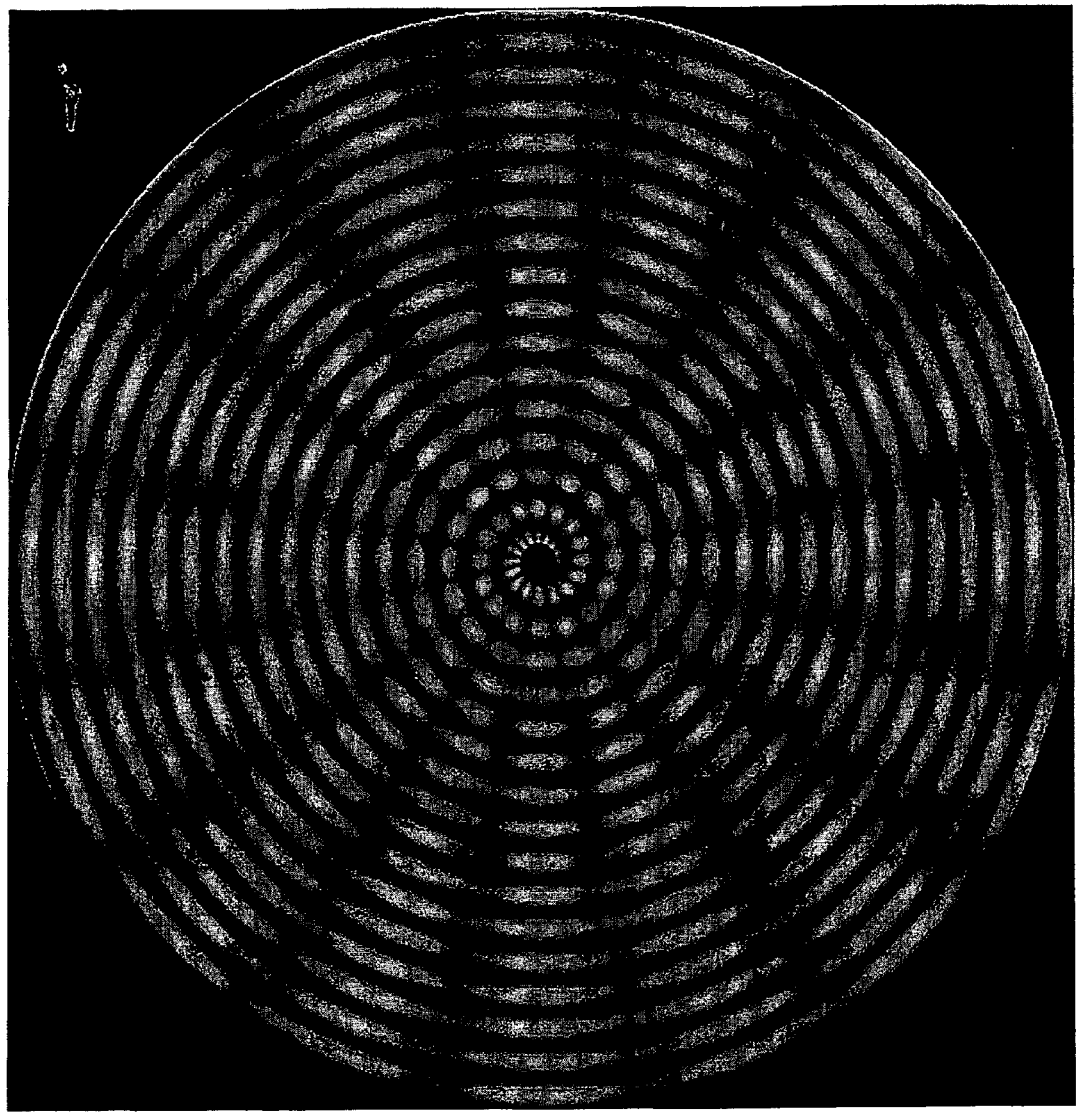
FIG. 6 shows an example of a reflection target pattern with the phase of the radial intensity profile varied over one cycle.

The center of the radial intensity profile is set to zero to correspond to the aperture at the reflective pattern source 2 indicated in FIG. 1. The profile is zero for radial distances up to r0 mm. For radial distance values from r0 to rMax, the radial intensity profile is a sinusoid. For radial distance values greater than rMax, the radial intensity profile is zero. This pattern of zero, sinusoid, zero, can be modeled as a rectangular function times a sinusoid. This is important because it facilitates analysis using Fourier transforms. The parameter Nr controls the number of cycles in the radial direction. For example, in FIG. 3 the intensity profile has 4 radial cycles. It also has r0=0.5 and rMax=5.0, which are reasonable design parameters for the pattern at the corneal surface. The final parameter, Nt is the number of times the intensity profile will spiral. This parameter will usually be 0 or 1. For Nt=0, the reflection pattern is axially symmetric as illustrated in FIG. 5. For Nt=1, one spiral of the radial intensity profile is generated as illustrated in FIG. 6.

Angular Color Profile

The angular color profile is given by equation (2).

$$RED(t) = \frac{\cos(t \times NRED + phiRED)}{2} + \frac{1}{2}$$

$$GRN(t) = \frac{\cos(t \times NGRN + phiGRN)}{2} + \frac{1}{2}$$

$$BLU(t) = \frac{\cos(t \times NBLU + phiBLU)}{2} + \frac{1}{2}$$

where

NRED, PhiRED=red cycles and phase

NGRN, PhiGRN=green cycles and phase

NBLU, PhiBLU=blue cycles and phase

Figure 4:
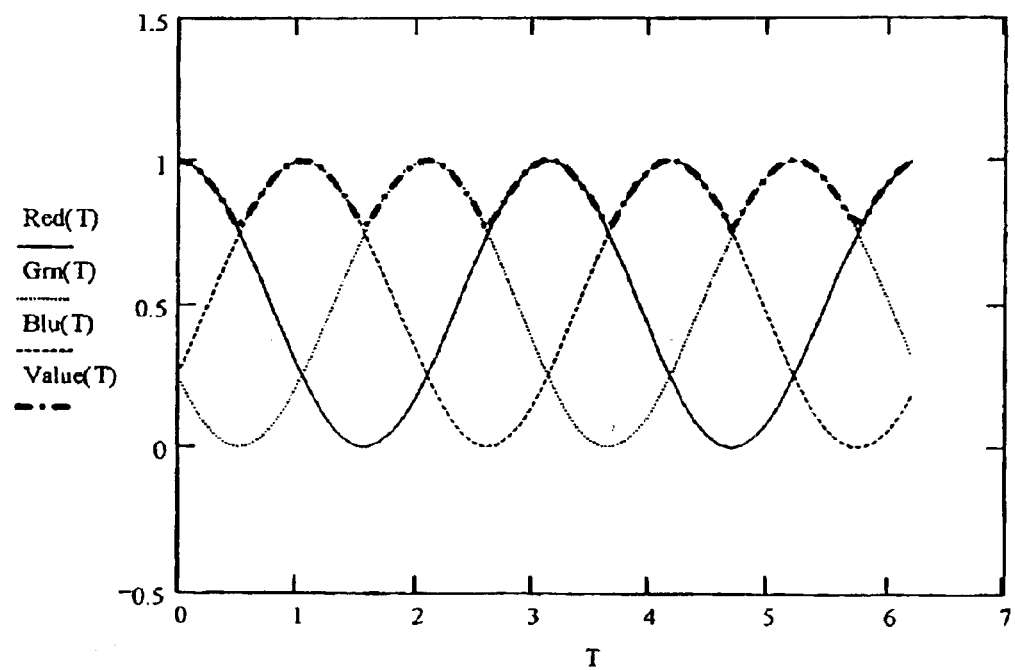
FIG. 4 show example graphs of the red, green, blue, and value functions for the reflection target pattern as a function of angle.

The angular color profile components RED(t), GRN(t), and BLU(t) correspond to the red, green, and blue magnitudes as a function of angle. In hue, saturation, and value (HSV) color space, the value is given by the maximum of the red, green, and blue components for a given color point. We prefer to set the phase values to 0, 2PI/3, and 4PI/3 for PhiRED, PhiGRN, and PhiBLU, respectively. FIG. 4 shows example profiles for RED(t), GRN(t), and BLU(t) and the correspond Value(t). To generate a monochrome pattern only, the values of NRED, PhiRED, NGRN, PhiGRN, NBLU, and PhiBLU are all set to zero.

Contrast Control

To control the contrast in the pattern we employ equation (3).

$$P(r, t) = (PMax - PMin) \times I(r, t) \times \begin{bmatrix} RED(t) \\ GRN(t) \\ BLU(t) \end{bmatrix} + PMin \quad (3)$$

where

P(r,t)=a vector of red, green, and blue components at (r,t)

PMax=maximum value of a color component

PMin=minimum value of a color component

I(r,t)=radial intensity profile from equation (1)

RED(t), GRN(t), BLU(t)=color profiles from equation (2)

Equation (3) computes the final red, green, and blue color components corresponding to a point (r,t) on the reflection pattern. To use the maximum contrast available for a pattern, PMax is set to the maximum and PMin is set to the minimum value for the display method. For example, for an 8-bit image, PMax and PMin are set to 255 and 0 to provide the maximum pattern contrast. Other contrast values may be desirable, depending upon the specific application.

To manufacture the reflection pattern source for a corneal topography system, several methods may be employed. One method is to develop a flat representation of the pattern that can be applied to a translucent cone shape. Another method is to directly apply colors to a suitable surface. To generate the pattern to be applied, the geometry illustrated in FIG. 1 is specified in a computer program and optical ray tracing is used to determine the color using equation (3), and the final pixel location for a flat image that is then applied to the reflection pattern structure. Other shapes are possible that permit a flat image to be applied to suitable shapes for the reflection pattern structure. These shapes include portions of a cylinder and polygonal structures.

An alternative set of reflection patterns could be generated by swapping the color and intensity directions. That is, the intensity profile could be generated for the meridional direction and the color profile for the radial direction.

Also, a point function to account for system non-linearity may be required to yield the best image quality. Various point functions are commonly employed for this purpose.

I claim:

1. A corneal topography system for measuring the shape of the cornea comprising a source of light for impinging on a cornea at a selected point and being reflected therefrom, a lens for focusing said reflected light onto a sensor at an image point, said image point of said reflected light having a radial intensity profile, an angular color profile and a contrast control, and means for correlating said image point with said selected point, and a reflection pattern source means for generating a continuous two dimensional reflection pattern using sinusoidal profiles of said intensity profile and said color profile.

2. A corneal topography system of claim 1 wherein said source of light is projected in a pattern and said reflection pattern source means correlates each of said image points with said selected points, respectively.

3. A corneal topography system of claim 1 wherein said intensity profile is determined by the formula $$I(r, t) = \begin{cases} 0 & r < r0 \\ \dfrac{\cos\left[\dfrac{(r - r0) \times 2\pi \times Nr}{rMax - r0} + t \times Nt + \pi\right]}{2} + \dfrac{1}{2} & r0 < r < rMax \\ 0 & r > rMax \end{cases}$$

where r0=radial starting point (mm), rMax=radial ending point (mm),

Nr=radial cycles, and

Nt=spiral cycles, said angular color profile comprises red, green and blue, said profile determined by the following formula $$RED(t) = \frac{\cos(t \times NRED + phiRED)}{2} + \frac{1}{2}$$

$$GRN(t) = \frac{\cos(t \times NGRN + phiGRN)}{2} + \frac{1}{2}$$

$$BLU(t) = \frac{\cos(t \times NBLU + phiBLU)}{2} + \frac{1}{2}$$

where

NRED, PhiRED=red cycles and phase,

NGRN, PhiGRN=green cycles and phase, and

NBLU, PhiBLU=blue cycles and phase, and said contrast control is determined by the formula $$P(r, t) = (PMax - PMin) \times I(r, t) \times \begin{bmatrix} RED(t) \\ GRN(t) \\ BLU(t) \end{bmatrix} + PMin \quad (3)$$

where

P(r,t)=a vector of red, green, and blue components at (r,t),

PMax=maximum value of a color component,

PMin=minimum value of a color component,

I(r,t)=radial intensity profile from equation (1), and

RED(t), GRN(t), BLU(t)=color profiles from equation (2).

4. A corneal topography system of claim 2 wherein said intensity profile is determined by the formula $$I(r, t) = \begin{cases} 0 & r < r0 \\ \dfrac{\cos\left[\dfrac{(r - r0) \times 2\pi \times Nr}{r\text{Max} - r0} + t \times Nt + \pi\right]}{2} + \dfrac{1}{2} & r0 < r < r\text{Max} \\ 0 & r > r\text{Max} \end{cases}$$

where
  r0=radial starting point (mm),
  rMax=radial ending point (mm),
  Nr=radial cycles, and
  Nt=spiral cycles,
said angular color profile comprises red, green and blue, said profile determined by the following formula $$RED(t) = \frac{\cos(t \times NRED + phiRED)}{2} + \frac{1}{2}$$

$$GRN(t) = \frac{\cos(t \times NGRN + phiGRN)}{2} + \frac{1}{2}$$

$$BLU(t) = \frac{\cos(t \times NBLU + phiBLU)}{2} + \frac{1}{2}$$

where
  NRED, PhiRED=red cycles and phase,
  NGRN, PhiGRN=green cycles and phase, and
  NBLU, PhiBLU=blue cycles and phase and
said contrast control is determined by the formula $$P(r, t) = (P\text{Max} - P\text{Min}) \times I(r, t) \times \begin{bmatrix} RED(t) \\ GRN(t) \\ BLU(t) \end{bmatrix} + P\text{Min} \quad (3)$$

where
  P(r,t)=a vector of red, green, and blue components at (r,t),
  PMax=maximum value of a color component,
  PMin=minimum value of a color component,
  I(r,t)=radial intensity profile from equation (1), and
  RED(t), GRN(t), BLU(t)=color profiles from equation (2).

5. A corneal reflection pattern source means comprising a continuous two-dimensional corneal topography pattern having a radial direction and an angular direction, said pattern including intensity and color sinusoidal profiles, said intensity profile and said color profile each having a range of amplitude, phase and spatial frequency.

6. A corneal reflection pattern source means of claim 5 wherein said radial direction contains sinusoidal intensity profile of a selected amplitude, phase, and spatial frequency in said range and said angular direction contains a sinusoidal color profile, said sinusoidal color profile including individual color components, each of said individual color components having a selected amplitude, phase, and spatial frequency in said range.

7. A corneal reflection pattern source means of claim 5 wherein said radial direction contains a sinusoidal color profile, said sinusoidal color profile including individual color components of a selected amplitude, phase, and spatial frequency in said range and said angular direction contains a sinusoidal intensity profile of a selected amplitude, phase, and spatial frequency in said range.

8. A corneal reflection pattern source means of claim 5 wherein said sinusoidal profiles have a radial direction and an angular direction, said phase of said radial sinusoid is constant over said angular direction to yield a pattern of concentric rings.

9. A corneal reflection pattern source means of claim 5 wherein said sinusoidal profiles have a radial direction and an angular direction, said phase of said of said radial sinusoid varies over said angular direction to yield a spiral pattern.

10. A corneal reflection pattern source means of claim 5 wherein said profiles are represented by powers of sinusoids.

11. A reflection pattern source means for use with a corneal topography system for correlating the location of a reflected light with the source of the light comprising a two dimensional surface, said surface having a circular pattern thereon for measuring reflected light from a cornea, said reflected light having a sinusoidal intensity profile and a sinusoidal color profile, said pattern being a function of said intensity profile and said color profile.

12. A refection pattern source means of claim 11 wherein intensity profile and said color profile are varied and said circular pattern is a series of concentric rings.

13. A reflection pattern source means of claim 11 wherein said intensity profile and said color profile are varied and said circular pattern is a spiral.

14. A reflection pattern source means of claim 12 wherein said intensity profile is determined by the formula $$I(r, t) = \begin{cases} 0 & r < r0 \\ \dfrac{\cos\left[\dfrac{(r - r0) \times 2\pi \times Nr}{r\text{Max} - r0} + t \times Nt + \pi\right]}{2} + \dfrac{1}{2} & r0 < r < r\text{Max} \\ 0 & r > r\text{Max} \end{cases}$$

where r0=radial starting point (mm),
  rMax=radial ending point (mm),
  Nr=radial cycles, and
    Nt=spiral cycles, said color profile comprises red, green and blue, said profile determined by the following formula $$RED(t) = \frac{\cos(t \times NRED + PhiRED)}{2} + \frac{1}{2}$$

$$GRN(t) = \frac{\cos(t \times NGRN + PhiGRN)}{2} + \frac{1}{2}$$

$$BLU(t) = \frac{\cos(t \times NBLU + PhiBLU)}{2} + \frac{1}{2}$$

where

NRED, PhiRED=red cycles and phase,
  NGRN, PhiGRN=green cycles and phase, and
  NBLU, PhiBLU=blue cycles and phase.

15. A reflection pattern source means of claim 13 wherein said intensity profile is determined by the formula $$I(r, t) = \begin{cases} 0 & r < r0 \\ \dfrac{\cos\left[\dfrac{(r - r0) \times 2\pi \times Nr}{r\text{Max} - r0} + t \times Nt + \pi\right]}{2} + \dfrac{1}{2} & r0 < r < r\text{Max} \\ 0 & r > r\text{Max} \end{cases}$$

where
- r0=radial starting point (mm),
- rMax=radial ending point (mm),
- Nr=radial cycles, and
- Nt=spiral cycles, said color profile comprises red, green and blue, said profile determined by the following formula $$RED(t) = \frac{\cos(t \times NRED + PhiRED)}{2} + \frac{1}{2}$$

$$GRN(t) = \frac{\cos(t \times NGRN + PhiGRN)}{2} + \frac{1}{2}$$

$$BLU(t) = \frac{\cos(t \times NBLU + PhiBLU)}{2} + \frac{1}{2}$$

where

NRED, PhiRED=red cycles and phase,
NGRN, PhiGRN=green cycles and phase, and
NBLU, PhiBLU=blue cycles and phase.

* * * * *